(12) United States Patent
Cao et al.

(10) Patent No.: US 9,993,397 B2
(45) Date of Patent: Jun. 12, 2018

(54) COMPOSITE PARTICLES AND COMPOSITIONS WITH COMPOSITE PARTICLES

(75) Inventors: Jian Cao, Shanghai (CN); Zhaoting Liu, Shanghai (CN); Xiaoyi Pang, Shanghai (CN); Robert Paul Velthuizen, Trumbull, CT (US); Xiuxia Wang, Shanghai (CN)

(73) Assignee: Conopco Inc., Englewood Cliffs, NJ (US)

( * ) Notice: Subject to any disclaimer, the term of this patent is extended or adjusted under 35 U.S.C. 154(b) by 652 days.

(21) Appl. No.: 13/885,721

(22) PCT Filed: Nov. 2, 2011

(86) PCT No.: PCT/EP2011/069224
§ 371 (c)(1),
(2), (4) Date: Jun. 5, 2013

(87) PCT Pub. No.: WO2012/069291
PCT Pub. Date: May 31, 2012

(65) Prior Publication Data
US 2013/0287826 A1 Oct. 31, 2013

(30) Foreign Application Priority Data
Nov. 23, 2010 (WO) ............... PCT/CN2010/001877

(51) Int. Cl.
*A61K 8/02* (2006.01)
*C08K 3/00* (2018.01)
*C08K 3/22* (2006.01)
*A61K 8/27* (2006.01)
*A61K 8/28* (2006.01)
*A61K 8/29* (2006.01)
*A61Q 19/00* (2006.01)
*A61K 8/81* (2006.01)
*A61K 8/19* (2006.01)
*C08K 9/10* (2006.01)

(52) U.S. Cl.
CPC .......... *A61K 8/0245* (2013.01); *A61K 8/0279* (2013.01); *A61K 8/19* (2013.01); *A61K 8/27* (2013.01); *A61K 8/28* (2013.01); *A61K 8/29* (2013.01); *A61K 8/8152* (2013.01); *A61Q 19/00* (2013.01); *C08K 3/0033* (2013.01); *C08K 3/22* (2013.01); *A61K 2800/412* (2013.01); *C08K 9/10* (2013.01)

(58) Field of Classification Search
CPC .................................................. A61K 8/0279
See application file for complete search history.

(56) References Cited

U.S. PATENT DOCUMENTS 5,223,559 A 6/1993 Arraudeau et al.
5,314,683 A 5/1994 Schlossman
5,356,617 A 10/1994 Schlossman
5,932,194 A 8/1999 Plessix et al.
5,972,359 A 10/1999 Sine et al.
5,997,890 A 12/1999 Sine
6,174,533 B1 1/2001 SaNogueira, Jr.
6,333,053 B1 12/2001 Simon
6,416,573 B2 7/2002 Horino et al.
6,491,929 B1 12/2002 Anderson et al.
6,511,672 B2 1/2003 Tan et al.
6,551,604 B1 4/2003 Beck
7,247,378 B2 7/2007 Kim et al.
7,709,013 B2 5/2010 Patel
2004/0071956 A1* 4/2004 Tsuji ..................... A61K 8/27
428/328
2004/0228886 A1 11/2004 Ding et al.
2004/0241118 A1 12/2004 Simon et al.
2005/0025730 A1 2/2005 Chevalier et al.
2005/0031658 A1 2/2005 Girier et al.
2005/0058677 A1 3/2005 Richard et al.
2005/0100568 A1 5/2005 De Mul et al.
2005/0118122 A1 6/2005 Simon et al.
2005/0118218 A1 6/2005 Cassin
2005/0163730 A1 7/2005 Rosevear et al.
2005/0175562 A1 8/2005 Hadasch et al.
2005/0203215 A1 9/2005 Ugazio
2005/0287092 A1 12/2005 Liechty et al.
2005/0288416 A1 12/2005 Lichtenstein et al.
2006/0257336 A1 11/2006 Ferrari et al.
2007/0160636 A1 7/2007 Kasai (Continued)

FOREIGN PATENT DOCUMENTS

CN 1216515 A 5/1999
CN 1225933 A 8/1999

(Continued)

OTHER PUBLICATIONS

Avon, U.S. Cosmetics presents elliptical polymethyl methacrylate, U.S. Cosmetics presents elliptical polymethyl methacrylate, p. 112, vol. 119 No. 10/Oct. 2004, US.
Impag, SH219-The Soft-Focus Additive, IMPAG Soft-focus-additive, DE.
Kikuchi, Hajime et al., Development of UV absorbent hollow organic microspheres, Development of UV absorbent hollow organic microspheres, 441-9, 1993 27(3), JP.
Lisa Bouldin et al., Control of skin tone via microlens technology, Control of skin tone via microlens technology, Dec. 2007, US.
Luo, Fusheng et al., Preparation and application in cosmetic of PMMA-TiO2 compounded microspheres, Preparation and application in cosmetic of PMMA-TiO2 compounded microspheres, 40-42, 2002, 32(2), CN.

(Continued)

*Primary Examiner* — Kyle A Purdy
(74) *Attorney, Agent, or Firm* — Greenberg Traurig, LLP

(57) ABSTRACT

Composite particles and compositions with the composite particles are described. The particles have a polymeric base with or without voids and subparticles whereby the subparticles have indexes of refraction above and below the index of refraction of the polymeric base. When typically applied, the compositions impart excellent soft focus results on the skin of consumers.

17 Claims, No Drawings

(56) References Cited

U.S. PATENT DOCUMENTS

| | | | |
|---|---|---|---|
| 2008/0008730 A1 | 1/2008 | De mul et al. | |
| 2008/0138366 A1 | 6/2008 | Okubo et al. | |
| 2008/0145435 A1 | 6/2008 | Richard et al. | |
| 2008/0152682 A1 | 6/2008 | Simoulidis et al. | |
| 2008/0219940 A1 | 9/2008 | Chevalier et al. | |
| 2008/0220026 A1 | 9/2008 | Maitra et al. | |
| 2008/0305069 A1 | 12/2008 | Cassin et al. | |
| 2009/0155321 A1 | 6/2009 | Harichian et al. | |
| 2010/0119829 A1* | 5/2010 | Karpov | C09C 1/407 428/407 |

FOREIGN PATENT DOCUMENTS

| | | |
|---|---|---|
| CN | 101181184 A | 5/2008 |
| CN | 101210120 A | 7/2008 |
| FR | 2869796 A | 11/2005 |
| JP | 11246357 A | 9/1999 |
| JP | 2001294513 | 10/2001 |
| JP | 2001294513 A | 10/2001 |
| JP | 2002029930 A | 1/2002 |
| JP | 2002154929 | 5/2002 |
| JP | 2003040737 A | 2/2003 |
| JP | 2003081768 A | 3/2003 |
| JP | 2004067624 A | 3/2004 |
| JP | 2005041948 | 2/2005 |
| JP | 2005154279 A | 6/2005 |
| JP | 2005194212 A | 7/2005 |
| JP | 2005263709 | 9/2005 |
| JP | 2006137704 | 6/2006 |
| JP | 2008161817 | 7/2008 |
| JP | 2008184435 | 8/2008 |
| WO | WO9852532 | 11/1998 |
| WO | WO9852533 | 11/1998 |
| WO | WO9852534 | 11/1998 |
| WO | WO9852535 | 11/1998 |
| WO | WO9956702 | 11/1999 |
| WO | WO0051551 | 9/2000 |
| WO | WO0051553 C2 | 9/2000 |
| WO | WO0152795 | 7/2001 |
| WO | WO0218498 | 3/2002 |
| WO | WO02056846 | 7/2002 |
| WO | WO02098349 | 12/2002 |
| WO | WO04050028 | 6/2004 |
| WO | WO05039522 | 5/2005 |
| WO | WO05056621 | 6/2005 |
| WO | WO05070382 | 8/2005 |
| WO | WO05094779 | 10/2005 |
| WO | WO05094780 | 10/2005 |
| WO | WO2005094780 A1 | 10/2005 |
| WO | WO2005094781 A1 | 10/2005 |
| WO | WO06049696 | 5/2006 |
| WO | WO06049697 | 5/2006 |
| WO | WO07057931 | 5/2007 |
| WO | WO07116003 | 10/2007 |
| WO | WO08030331 | 3/2008 |
| WO | WO08079559 | 7/2008 |
| WO | WO08079560 | 7/2008 |
| WO | WO08079758 | 7/2008 |
| WO | WO08079760 | 7/2008 |
| WO | WO2008077728 A2 | 7/2008 |
| WO | WO09085444 A1 | 7/2009 |
| WO | WO10019164 | 2/2010 |
| WO | WO08079543 | 7/2013 |
| WO | WO09088584 | 7/2013 |
| WO | WO05095571 | 10/2013 |

OTHER PUBLICATIONS

International Search Report, PCT/EP2011/069224, dated Jan. 30, 2012, 3 pp.

International Search Report, PCT/CN2010/011877, dated Sep. 1, 2011, 5 pp.

Delrieu, et al., In-vitro Method for Quantification of Soft Focus Effect of Particulates, NYSCC Scientific Meeting, Dec. 8, 2005, 1-33, US.

* cited by examiner

COMPOSITE PARTICLES AND COMPOSITIONS WITH COMPOSITE PARTICLES

FIELD OF THE INVENTION

The present invention is directed to composite particles as well as compositions comprising the composite particles. More particularly, the composite particles comprise a polymeric base that comprises a subparticle having an index of refraction above the index of refraction of the polymeric base as well as subparticle and/or void having an index of refraction below the index of refraction of the polymeric base. The compositions comprising the composite particles have excellent sensory characteristics, and surprisingly, exhibit a measurably and significantly higher soft focus than conventional light scattering particles that impart an improved appearance to consumers topically applying the same.

BACKGROUND OF THE INVENTION

Many consumers desire to look younger and reduce the visibility of blemishes, fine lines and wrinkles, especially on their face and hands. Such a desire is coupled with the fact that consumers want to look radiant and natural in the absence of having an artificial matte look typically provided by traditional foundation-based products which tend to be overly opaque in nature and may have aesthetic and/or cultural negatives.

Attempts at "perfecting" skin have been made. Often, topical compositions with absorbent fillers (e.g., talc, silica, kaolin) are made wherein such inorganic fillers hide skin imperfections by absorbing some light and simply reflecting light back not unlike paint. An alternative approach is referred to as achieving a soft focus effect. This occurs when incoming light is distorted by scattering (dispersion) wherein light is twisted into a variety of directions. Soft focus is often thought of as a measure similar to haze but applicable to thin product films. Traditional approaches, unfortunately, either hide imperfections in the absence of radiance or result in radiance and healthy glow but with aesthetically displeasing skin appearance, for example, through enhanced visibility of skin topography.

There is an increasing interest to develop composite particles and compositions with composite particles that yield an excellent soft focus. This invention, therefore, is directed to composite particles and compositions comprising such composite particles that are expected to result in excellent sensory characteristics, and surprisingly, impart superior soft focus results. The composite particles comprise a polymeric base and subparticles with or without voids, some of which have indexes of refraction above and some of which have indexes of refraction below the index of refraction of the polymeric base.

Additional Information

Efforts have been disclosed for making compositions that impart a soft focus. In U.S. Patent application No. 2008/0152682, single-crystal platy barium sulfate containing compositions are described.

Still other efforts have been disclosed for making topical compositions that improve skin characteristics. In U.S. Patent Application Nos. 2005/0100568 and 2009/0155321, cosmetic compositions for improving skin appearance are described.

Even other efforts have been disclosed for making topical compositions that improve skin characteristics. In U.S. Pat. Nos. 5,972,359, 5,997,890 and 6,174,533, topical compositions for covering skin imperfections are described.

None of the additional information above describes a composite particle and composition as claimed in this invention.

SUMMARY OF THE INVENTION

In a first aspect, the present invention is directed to a composite particle comprising:
(a) a polymeric base;
(b) a subparticle having an index of refraction above the index of refraction of the polymeric base; and
(c) a subparticle, void or both having an index or indexes of refraction below the index of refraction of the polymeric base.

In a second aspect, the present invention is directed to a composition comprising the composite particle of the first aspect of this invention.

In a third aspect, the present invention is directed to a method for improving skin characteristics by applying to the skin the composition of the second aspect of this invention.

All other aspects of the present invention will more readily become apparent upon considering the detailed description and examples which follow.

Skin, as used herein, is meant to include skin on the face, neck, chest, back, arms, hands, legs, buttocks and scalp. Subparticle, as used herein, is meant to mean a particle that is smaller than the composite particle but a component thereof. Composite particle and subparticle are preferably meant to be spherical particles, whereby the diameter of the subparticles can often range from 10 to 2,100 times smaller than the diameter of the composite particle. Subparticle is meant to be dispersed throughout the polymeric base. To the extent perfect spheres are not formed, diameter is meant to mean the longest cross-sectional distance measurable on particle. Void, as used herein, means a gap, space or pocket filled with vacuum or air, and preferably, obtained via the use of a porogen like ethyl acetate. Such a void may be used with or in lieu of the subparticle having an index of refraction below the index of refraction of the polymeric base. Low and below, and high and above may be used interchangeably to describe the low index of refraction subparticles and the high index of refraction subparticles, respectively. The diameter of composite particle may be measured, for example, by scanning electron microscopy (SEM). The diameter of subparticle and/or void may be measured, for example, by transmission electron microscopy (TEM). The index of refraction may be determined by a conventional method in the art, preferably with light having a wavelength of 589 nm and at 25° C.

Comprising, as used herein, is meant to include consisting essentially of and consisting of. All ranges identified herein are meant to include all ranges subsumed therein if, for example, reference to the same is not explicitly made.

DETAILED DESCRIPTION OF THE PREFERRED EMBODIMENTS

The only limitations with respect to the polymeric base that may be used in this invention are that the base is one which is suitable for use in compositions that are topically applied and has an index of refraction that is in between the refraction indexes of the subparticles used. Often, the polymeric base is one having an index of refraction from 1.3 to 1.8, and preferably, from 1.4 to 1.7, and most preferably from 1.45 to 1.7, including all ranges subsumed therein. In an often preferred embodiment, the polymeric base used in this invention is one which may be derived from monomers suitable to undergo free radical polymerization.

Illustrative yet non-limiting examples of the types of monomers that may be used in this invention to polymeric base include styrene and derivatives thereof like 1-methyl-4-vinylbenzene, 1-tert-butyl-4-vinylbenzene, 1-bromo-4-vinylbenzene, 1-methoxy-4-vinylbenzene, 4-vinylbenzene acetate, and acrylates like 2-hydroxyethyl acrylate (HEA), tert-butyl acrylate (t-BA), methyl methacrylate (MMA), 2-(dimethylamino)ethyl methacrylate (DMAEMA), 2-hydroxyethyl methacrylate (HEMA), glycidyl methacrylate (GMA), and acrylamides like dimethylacrylamide (DMA), N-isopropylacrylamide (NIPAM), and acrylic acid and derivatives thereof, like methacrylic acid, and acrylonitriles, like methacrylonitrile, and dienes like 4-vinylpyridine (4VP), vinyl propionate, vinyl butyrate, vinyl ether, allybutyl ether, allylglycidyl ether, maleic acid, vinyl acetate as well as copolymers of the same and miscible and immiscible blends of polymers resulting form the same. In an especially preferred embodiment, the monomer employed is methyl methacrylate and the polymeric base is poly(methyl methacrylate).

In another especially preferred embodiment, the polymeric base has an index of refraction that is from 30 to 80%, and preferably, from 35 to 60% higher than the index of refraction of the subparticle used that has a lower index of refraction than the polymeric base, and an index of refraction that is from 10 to 50%, and preferably, from 15 to 45% lower than the index of refraction of the subparticle used that has a higher index of refraction than the polymeric base.

A crosslinking agent may optionally be used when a more dense composite particle is desired. Suitable crosslinking agents that may be used include, for example, divinylbenzene, 1,4-divinyloxylbutane, divinylsulfone, diallylphthalate, diallylacrylamide, tirallylisocyanurate, triallyltrimellitate, ethylene glycol dimethacrylate, propylene glycol dimethacrylate, pentaerythritol tetramethacrylate, pentaerythritol triamethacrylate, pentaerythritol dimethacrylate, trimethylolpropane tirmethacrylate, dipentaerythritol hexamethacrylate, dipentaerythritol pentamethacrylate, glycerol trimethacrylate, mixtures thereof or the like. When used, the crosslinking agent most preferred is ethylene glycol dimethacrylate. Typically, if used, crosslinking agent makes up from 0.01 to 20, and preferably, from 0.1 to 15, and most preferably, from 0.5 to 10% by weight based on the total weight of the polymeric base.

Often, the polymeric base (in the absence of a crosslinking agent) has a molecular weight ($M_n$) from 75,000 to 1.2 million, and preferably, from 100,000 to 800,000, and most preferably, from 400,000 to 600,000, including all ranges subsumed therein. Such a base is commercially available from suppliers like Sigma-Aldrich.

The subparticle having an index of refraction higher than the index of refraction of the polymeric base (e.g., and index of refraction from 1.65 to 3.0, and preferably, from 1.7 to 2.8, and most preferably, from 1.9 to 2.6, including all ranges subsumed therein) is limited only to the extent that the same may be used in a composition meant for topical application. Illustrative examples of the types of subparticles having an index of refraction higher than the index of refraction of the polymeric base are zinc oxide, titanium dioxide, zirconium oxide, iron oxide or mixtures thereof. Typically, such subparticles have a diameter from about 20 to 800 nm, and preferably, from 25 to 500 nm, and most preferably, from 30 to 400 nm, including all ranges subsumed therein.

The amount of such high index of refraction subparticle used typically ranges from 0.1 to 35%, and preferably, from 0.3 to 25%, and most preferably, from 8 to 20% by weight, based on total weight of the composite particle and including all ranges subsumed therein.

Regarding the subparticle having an index of refraction lower than that of the polymeric base, the same typically has an index of refraction from 1 to 1.4, and preferably, from 1 to 1.35, and most preferably, from 1.0 to 1.3, including all ranges subsumed therein. Illustrative examples of such subparticles include particles encapsulating air, gas or vacuum or mixtures thereof. Typically, such subparticles have a diameter from about 50 to 800 nm, and preferably, from 60 to 700 nm, and most preferably, from 70 to 600 nm including all ranges subsumed therein.

These subparticles can have a shell (e.g., clad or encapsulant) with one or more non-ionic ethylenically unsaturated momoners. Optionally, one or more monoethylenically unsaturated monomers containing at least one carboxylic acid group may be polymerized in the shell, such as, for example, acrylic acid, methacrylic acid, acryloxypropionic acid, methacryloxypropionic acid, acotinic acid, maleic acid, furmaric acid, itaconic acid, citraconic acid, copolymers thereof and derivatives thereof. Preferred carboxylic acid containing monomers are acrylic acid and methacrylic acid. When present in the shell, the same typically comprises from 0.1 to 12% by weight carboxylic acid containing monomer.

It is within the scope of the invention to optionally include in the shell one or more monoethylenically unsaturated monomers free of carboxylic acid groups. These include, for example, allylsulfonic acid, allylphosphonic acid, allyloxybenzene sulfonic acid, 2-methyl-2-propene-1-sulfonic acid, vinylsulfonic acid, styrenesulfonic acid, 2-acrylamido-2-methyl-propanesulfonic acid as well as derivatives and copolymers thereof. These monomers, when present, typically make up from 0.1 to 12% by weight of the total weight of the shell.

Other unsaturated monomers useful in preparing the shell polymer include, for example, vinyl acetate, acrylonitrile, methacrylonitrile, nitrogen containing ring compound unsaturated monomers, vinylaromatic monomers, ethylenic monomers and selected (meth)acrylic acid derivatives. Preferably the shell portion of the subparticles comprises as polymerized units from 0.001 to 90% (meth)acrylic acid derivative monomer and from 0.001 to 80% vinylaromatic monomer, based on total weight of the shell portion.

Often, the shell of the low index of refraction particle comprises, as polymerized units, from 5 to 95%, and preferably, from 10 to 80%, and most preferably, from 20 to 70% based on total weight of the shell portion, of (meth)acrylic acid derivative monomer selected from one or more of methyl acrylate, methyl methacrylate, ethyl acrylate, ethyl methacrylate, butyl acrylate, butyl methacrylate, isobutyl acrylate, isobutyl methacrylate, hydroethyl methacrylate, hydroxypropyl methacrylate, dimethylaminoethyl methacrylate and dimethylaminopropyl methacrylamide.

Suitable vinylaromatic monomers for use as shell in the low index of refraction particles include, for example, styrene, alpha-methylstyrene, vinyltoluene, alkyl-substituted styrene (such as t-butylstyrene and ethylvinylbenzene), halogenated styrenes (such as chlorostyrene and 3,5-bis (trifluoromethyl)styrene), ethylvinylbenzene, t-butylstyrene and copolymers thereof. When present in the shell polymer, the amount of vinylaromatic monomer units is often from 1 to 85%, and preferably, from 5 to 75%, and most preferably, from 10 to 50%, based on total weight of the shell portion of the polymer particles.

Examples of nitrogen-containing unsaturated ring compound monomers suitable for use include vinylpyridine, 2-methyl-5-vinylpyridine, 2-ethyl-5-vinylpyridine, 3-methyl-5-vinylpyridine, 2,3-dimethyl-5-vinylpyridine, 2-methyl-3-ethyl-5-vinylpyridine, methyl-substituted quinolines and soquinolines, 1-vinylimidazole, 2-methyl-1-vinylimidazole, N-vinylcaprolactam, N-vinylbutyrolactam and N-vinylpyrrolidone and copolymers.

Additional suitable monomers that may be used to make shell for the low index of refraction particles used in the composition of this invention include ethylenic monomers, (like, for example, ethylene, propylene, isobutylene, long chain alkyl alpha-olefins (such as $C_{10}$-$C_{20}$ alkyl α-olefins), vinyl halides (such as vinyl chloride, vinyl fluoride, vinyl bromide), vinylidene halides (such as vinylidene chloride and vinylidene fluoride), partially halogenated (meth)acrylates (such as 2-(perfluorododecyl)ethyl acrylate, 2-(perfluorododecyl)ethyl methacrylate, 2-(perfluorohexyl)ethyl acrylate, 2-(perfluorohexyl)ethyl methacrylate, hexafluoroisopropyl methacrylate, 2,2,3,3-tetrafluoropropyl acrylate and 2,2,2-trifluoroethyl methacrylate, and partially halogenated alkenes (such as 1,1,1-trifluoro-2,2-(trifluoromethyl)-butene). Such subparticles are commercially available wherein the preferred for use herein are made commercially available by Rohm and Haas under the SunSphere™ name.

The amount of such low index of refraction subparticle used typically ranges from 0.1 to 20%, and preferably, from 0.2 to 10%, and most preferably, from 0.3 to 6% based on total weight of the composite particle and including all ranges subsumed therein. Polymerization may be enhanced with initiators like benzoyl peroxide.

In another especially preferred embodiment, pore forming agents or porogens like, for example, cyclohexanol, toluene, 2-ethylhexanoic acid, dibutylphthalate, 1-methyl-2-pyrrolidone, 1-decanol, heptane, silicone oil, poly(alkylene) glycol, ethyl acetate, mixtures thereof or the like may be used during the process for making the composite particle of this invention. Such porogens may be removed with a solvent and/or heat to yield void within the composite particle. Such voids, which will have an index of refraction below the index of refraction the polymeric base, and may be used with or in lieu of subparticle having an index of refraction below the index of refraction of the polymeric base. When voids are present, they are expected to have dimensions that are consistent with the dimensions of the subparticles having an index of refraction below the index of refraction of the polymeric base. Moreover, the total amount of void within the polymeric base when used alone or in combination with low index of refraction subparticle is typically from 0.1 to 30%, and preferably, 0.5 to 20%, and most preferably, from 1 to 8% by volume, based on total volume of polymeric base and including all ranges subsumed therein.

In an especially preferred embodiment, composite particle (preferably manufactured in situ), typically has a diameter from 0.5 to 75 microns, and preferably, from 1 to 50 microns, and most preferably, from 4 to 20 microns, including all ranges subsumed therein.

When making composition, the same typically comprises from 0.1 to 20%, and preferably, from 0.2 to 15%, and most preferably from, 0.75 to 6% by weight composite particle, based on total weight of the composition and including all ranges subsumed therein.

A variety of materials may be present in the compositions comprising the composite particles of this invention to serve as cosmetically acceptable carriers. Such carriers may, for example, be water-in-oil, oil-in-water emulsions where the oil-in-water type is preferred. Foremost is water as a carrier. Amounts of water may range from about 1 to about 90%, preferably from about 30 to about 80%, optimally from about 50 to about 70% by weight of the composition.

Emollient materials may be included as carriers in compositions of this invention. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature (20-25° C.). Volatile silicone oils are preferably chosen from cyclic (cyclomethicone) or linear polydimethylsiloxanes containing from 3 to 9, preferably from 4 to 5, silicon atoms. In many liquid versions of compositions according to the present invention, the volatile silicone oils may form a relatively large component of the compositions as carriers. Amounts may range from about 5% to about 80%, preferably from about 20% to about 70% by weight of the composition.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m²/s at 25° C. Among the preferred nonvolatile emollients useful in the present compositions are the polydimethyl siloxanes having viscosities from about $1 \times 10^{-s}$ to about $4 \times 10^{-4}$ m²/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44). Amounts of the aforementioned silicone elastomers will usually be present from 0.1 to 20% by weight dissolved usually in a volatile silicone oil such as cyclomethicone.

When silicones are present in large amounts as carrier and water is also present, the systems may be oil continuous. These normally will require emulsification with a water-in-oil emulsifier such as a dimethicone copolyol (e.g. Abil EM-90 which is cetyl dimethicone copolyol).

Among the ester emollients are:

a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oleyl myristate, oleyl stearate, and oleyl oleate.

b) Ether-esters such as fatty acid esters of ethoxylated fatty alcohols.

c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate.

d) Wax esters such as beeswax, spermaceti wax and tribehenin wax.

e) Sterols esters, of which cholesterol fatty acid esters are examples thereof.

f) Sugar ester of fatty acids such as sucrose polybehenate and sucrose polycottonseedate.

Of particular use also are the $C_{12-15}$ alkyl benzoate esters sold under the Finsolve brand.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range anywhere from 0.5 to 50%, preferably between 1 and 15% by weight of the composition. Most preferred is glycerol (also known as glycerin). Amounts of glycerin may range from about 1% to about 50%, preferably from 10 to 35%, optimally from 15 to 30% by weight of the composition.

Besides cosmetically acceptable carriers, the compositions of this invention may include a variety of other functional ingredients. Sunscreen actives may be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzone, available as Parsol 1789®, Dermablock OS® (octylsalicylate) and Mexoryl SX® (with INCI name of Terephthalylidene Dicamphor Sulfonic Acid).

Amounts of the organic sunscreen agent may range from about 0.1 to about 15%, preferably from about 0.5% to about 10%, optimally from about 1% to about 8% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range from about 0.05 to about 10%, preferably from about 0.3 to about 2% by weight of the compositions.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, butyl paraben, isobutyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins and flavonoids. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. A particularly suitable Vitamin $B_6$ derivative is Pyridoxine Palmitate. Among the preferred flavonoids are glucosyl hesperidin and rutin. Total amount of vitamins or flavonoids when present in compositions according to the present invention may range from 0.001 to 10%, preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are pomegranate, white birch (*Betula Alba*), green tea, chamomile, licorice, boswellia serrata, olive (*Olea Europaea*) leaf, arnica montana flower, lavandula angustifolia, and extract combinations thereof. The extracts may either be water soluble or water-insoluble carried in a solvent which respectively is hydrophilic or hydrophobic. Water and ethanol are the preferred extract solvents.

Miscellaneous other adjunct cosmetic ingredients that may be suitable for the present compositions include ceramides (e.g. Ceramide 3 and Ceramide 6), conjugated linoleic acids, colorants (e.g. iron oxides), metal (manganese, copper and/or zinc) gluconates, allantoin, palmitoyl pentapeptide-3, amino acids (e.g. alanine, arginine, glycine, lysine, proline, serine, threonine, glumatic acid and mixtures thereof), trimethylglycine, sodium PCA, chelator like disodium EDTA, opacifiers like titanium dioxide, magnesium aspartate, and combinations thereof. Amounts may vary from 0.000001 to 3% by weight of the composition.

A small amount of emulsifying surfactant may be present. Surfactants may be anionic, nonionic, cationic, amphoteric and mixtures thereof. Levels may range from 0.1 to 5%, preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present. Emulsifiers like PEG-100 stearate may be used as well as emulsion stabilizers like cetearyl alcohol and ceteareth-20 may be used and typically in amounts that do not exceed 5 percent by weight of the composition.

Other optional additives suitable for use in the composition of this invention include cationic ammonium compounds to enhance moisturization. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, optional additives for use with the same are moisturizing agents such as substituted ureas like hydroxymethyl urea, hydroxyethyl urea, hydroxypropyl urea; bis(hydroxymethyl) urea; bis (hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra (hydroxymethyl) urea; tetra(hydroxyethyl) urea; tetra (hydroxypropyl) urea; N-methyl-N'-hydroxyethyl urea; N-ethyl-N'-hydroxyethyl urea; N-hydroxypropyl-N'-hydroxyethyl urea and N,N' dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance. Such substituted ureas, while desirable in moisturizing formulations, are only selected for use when compatible with the desired sunless tanning agent or agents used in the compositions of this invention.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the composition and including all ranges subsumed therein When making the compositions of this invention, ingredients are typically mixed with moderate shear under atmospheric conditions. The compositions may be applied topically and typically 1-4 milligrams of composition is applied per square centimeter. Typically, the compositions display a pH from 4 to 6. Packaging for the composition of this invention can be a jar or tube as well as any other format typically seen for cosmetic, cream, washing and lotion type products.

The following examples are provided to facilitate an understanding of the invention. The examples are not intended to limit the scope of the claims.

Example 1

Composite particles of this invention were prepared in the following process.

Zinc oxide, MZY-303S (made commercially available by TAYCA Corporation), silicon processed particle having a size of about 35 nm, was employed as the subparticle having an index of refraction of about 2.0. The amount of zinc oxide used was varied from 0, 5, 10, 15, 20, 25, 30, and 35 percent by weight based on total weight of the composite particle. Methyl methacrylate was used as monomer to produce polymeric base. As a crosslinking agent, ethylene glycol dimethacrylate was added in an amount of 10 percent by weight based on the weight of monomer used. Benzoyl peroxide was used (1 percent by weight) as an initiator agent. Ethyl acetate was used as a porogen (weight ratio of ethyl acetate:monomer about 1:2). The zinc oxide particles were dispersed into the mixture of methyl methacrylate, ethylene glycol dimethacrylate, benzoyl peroxide, and ethyl acetate by sonification at room temperature. The resulting mixture was poured into 2 percent by weight poly (vinyl-alcohol) aqueous solution and emulsified with homogenization under 6,000 rpm of shear stress for 5 minutes. Polymerization was carried out in the glass reactor equipped with a stirrer, a reflux condenser and nitrogen gas inlet system. Agitation speed was fixed at 300 rpm throughout the process. Reaction temperature was 75° C., and reaction time was 5 hours. After completion, the resulting product was centrifuged to remove residue reagents by washing with ethanol and distilled water several times and drying under vacuum to obtain zinc oxide-polymethyl methacrylate-hollow (i.e., void containing) composite particles as powders consistent with this invention and having about 10 percent by volume voids. The particles obtained were suitable for formulating into end use consumer products such as lotions and creams.

Example 2

A procedure similar to the one described in Example 1 was repeated, except that BASF provided Z-cote HP1 zinc oxide particles (surface treated with triethoxycaprylylsilane) were used in lieu of MZY-3035 to produce zinc oxide-polymethyl methacrylate-hollow composite particles consistent with this invention.

Example 3

A procedure similar to the one described in Example 1 was repeated, except that KOBO provided ZnO-C-DMC2 zinc oxide particles were used in lieu of MZY-3035 to produce zinc oxide-polymethyl methacrylate-hollow composite particles consistent with this invention.

Example 4

A procedure similar to the one described in Example 1 was repeated, except that SunSphere™ hollow spheres provided by Rohm and Haas were used in lieu of porogen created voids to produce zinc oxide-polymethyl methacrylate-hollow composite particles consistent with this invention. The amount of hollow spheres used varied from 0, 1, 3, 5, 7, 10, 15, and 20 weight percent, with the low to high amounts being respectively matched to the low to high amounts of zinc oxide used in the composite particle made in Example 1.

Example 5

A procedure similar to the one described in Example 1 was repeated, except that titanium dioxide MT-700Z (provided by TAYCA Corporation) particles were used in lieu of zinc oxide to produce titanium dioxide-polymethyl methacrylate-hollow composite particles consistent with this invention.

Example 6

A procedure similar to the one described in Example 1 was repeated except that titanium dioxide TR-10 (provided by MIYOSHI KASEI) particles were used in lieu of zinc oxide to produce titanium dioxide-polymethyl methacrylate-hollow composite particles consistent with this invention.

Example 7

A procedure similar to the one described in Example 1 was repeated except that iron oxide Unipure Red LC 381 AS-EM (provided by SENSIENT) particles were used in lieu of zinc oxide to produce iron oxide-polymethyl methacrylate-hollow composite particles consistent with this invention.

Example 8

A procedure similar to the one described in Example 1 was repeated except that a 50:50 weight ratio of zinc oxide and titanium dioxide was used in lieu of only zinc oxide to yield zinc oxide-titanium dioxide-polymethyl methacrylate-hollow composite particles consistent with this invention. The amount of mixture of zinc oxide and titanium dioxide powders used was consistent with the amounts described in Example 1.

Example 9

A procedure similar to the one described in Example 1 was repeated except that a 50:50 weight ratio of zinc oxide and iron oxide was used to yield zinc oxide-iron oxide-polymethyl methacrylate-hollow composite particles consistent with this invention. The mixture of zinc oxide and iron oxide powders used were consistent with the amounts described in Example 1.

Example 10

Compositions (oil-in-water emulsions) comprising the composite particles of this invention and commercially available particles (see Table 1) were formulated. The compositions are provided in Table 2.

The composite particles of Example 1 (10% by weight zinc oxide) were completely dispersed in the oil phase with the additional ingredients and mixed thoroughly. The resulting oil-based mixture was gradually added to the aqueous phase. The resulting mixture was emulsified under 9,000 rpm of shear stress for 10 minutes and gradually stirred and cooled to room temperature.

TABLE 1

| No. | Brand Name | Composition | Suppliers |
| --- | --- | --- | --- |
| 1 | BPD 500W | HDI/Trimethylol Hexyllactone Crosspolymer and Silica | KOBO |
| 2 | EA209 | Ethylene/Acrylates Copolymer | KOBO |
| 3 | Ganzpearl 0820 | Microporous Poly(methyl Methacrylates) | Ganz |

TABLE 2

| Materials | Formulation (wt %) | Comparative Formulation 1 (wt %) | Comparative Formulation 2 (wt %) | Comparative Formulation 3 (wt %) |
| --- | --- | --- | --- | --- |
| Isohexadecane | 0.5 | 0.5 | 0.5 | 0.5 |
| Cetearyl alcohol & ceteareth-20 | 3.0 | 3.0 | 3.0 | 3.0 |
| Stearic acid | 0.2 | 0.2 | 0.2 | 0.2 |
| Dimethicone | 5.0 | 5.0 | 5.0 | 5.0 |
| PEG-100 stearate | 2.0 | 2.0 | 2.0 | 2.0 |
| Ethylhexylmethoxycinnamate | 7.0 | 7.0 | 7.0 | 7.0 |

TABLE 2-continued

| Materials | Formulation (wt %) | Comparative Formulation 1 (wt %) | Comparative Formulation 2 (wt %) | Comparative Formulation 3 (wt %) |
|---|---|---|---|---|
| Aristoflex AVC | 1.0 | 1.0 | 1.0 | 1.0 |
| TiO2 | 2.0 | 2.0 | 2.0 | 2.0 |
| ZnO-PMMA-Hollow | 5.0 | — | — | — |
| EA209 | — | — | 5.0 | — |
| Ganzpearl 0820 | — | 5.0 | — | — |
| PPD500W | — | — | — | 5.0 |
| Butylene glycol | 5.0 | 5.0 | 5.0 | 5.0 |
| Disodium EDTA | 0.1 | 0.1 | 0.1 | 0.1 |
| Glydant plus liquid | 0.2 | 0.2 | 0.2 | 0.2 |
| Niacinamide | 2.0 | 2.0 | 2.0 | 2.0 |
| Water | Balance | Balance | Balance | Balance |

A 75 micron thick film of composition was applied to a glass slide with a cube film applicator (Sheen 1103). The bi-directional reflectance and transmittance distribution function of the films was detected with a goniometer via a method similar to the one described in U.S. Patent Application No. 2008/0152682. Soft focus (SF) was calculated using the formula:

$$SF = \int_{ST+9}^{ST+90} T(\theta)d\theta \bigg/ \int_{ST}^{ST+90} T(\theta)d\theta$$

T ($\theta$) is the transmittance at angle $\theta$; ST is the specular transmittance angle. The incident angle was set at 48°.

All soft focus values were measured under same temperature (22° C.) and same humidity (45%) in a constant temperature and humidity room.

The soft focus results set forth in Table 3 unexpectedly show that compositions comprising the composite particles of this invention display better soft focus results when compared to compositions comprising conventional particles.

TABLE 3

| Particle | Soft Focus |
|---|---|
| EA209 | 0.22 |
| BPD 500W | 0.33 |
| Ganzpearl 0820 | 0.38 |
| Composite particle | 0.56 |

Example 11

Composite particles similar to the ones made in Example 1 were added to commercial creams. The commercial products are listed in Table 4.

The composite particles (5% by weight) were completely dispersed in the commercial creams at 60° C. The resulting product was emulsified under 9,000 rpm of shear stress for 10 minutes and gradually stirred to cool to the room temperature.

TABLE 4

| No. | Commercial Product |
|---|---|
| 1 | NIVEA ® sparking white day cream |
| 2 | Olay ® total effect UV protection treatment SPF 15 |

Soft focus for the products was determined via the method described in Example 10. The results indicate that the composite particles of this invention can improve the soft focus of NIVEA day cream by about 200% after 10 minutes and Olay total effect by about 225% after 2 hours.

Example 12

A first set of commercially available topical compositions similar to the ones described in Table 4 were charged with zinc oxide (0.5% by weight), SunSphere™ hollow spheres (0.25% by weight) and polymethyl methacrylate (4.25% by weight) as individual additives.

A second set of identical compositions were charged with the same ingredients except that the zinc oxide, hollow spheres and polymethyl methacrylate were in the form of a composite particle made via a method similar to the one described in Example 4. Soft focus for the two sets of compositions was assessed according to the method set out in Example 10.

The results unexpectedly show that, after two hours, the soft focus of the compositions made consistent with this invention was about five times better than the compositions having particles added as individual additives.

The invention claimed is:
1. A composite particle comprising:
 (a) a polymeric base;
 (b) a subparticle having
   an index of refraction above the index of refraction of the polymeric base and a shell,
     wherein the shell of the subparticle comprises
       a plurality of polymerized units, comprising at least one of:
         non-ionic ethylenically unsaturated monomers,
         monoethylenically unsaturated monomers containing at least one carboxylic acid group,
         monoethylenically unsaturated monomers free of carboxylic acid groups, and
         other unsaturated monomers;
 (c) from 0.1 to 20% by weight of the composite particle of a subparticle having an index of refraction below the index of refraction of the polymeric base, and
 (d) from 1 to 20% by volume of the polymeric base of void having an index of refraction below the index of refraction of the polymeric base.
2. The composite particle according to claim 1 wherein from 50 to 100 wt. % of the subparticle having an index of refraction above the index of refraction of the polymer base is dispersed inside the polymeric base.
3. The composite particle according claim 1 wherein the subparticle has a diameter of from 10 to 2,100 times smaller than the diameter of the composite particle.
4. The composite particle according to claim 1 wherein the polymeric base has an index of refraction from 1.3 to 1.8.
5. The composite particle according to claim 1 wherein the polymeric base has an index of refraction that is 30 to 80% above the index of refraction of the void that has an index of refraction below the index of refraction of the polymeric base, and has an index of refraction that is 10 to

50% below the index of refraction of the subparticle that has an index of refraction above the index of refraction of the polymeric base.

6. The composition particle according to claim 4 wherein the polymeric base is poly(methyl methacrylate).

7. The composite particle according to claim 1 wherein the subparticle having an index of refraction above the index of refraction of the polymeric base is zinc oxide, titanium dioxide, zirconium oxide, iron oxide or a mixture thereof.

8. The composite particle according to claim 1 wherein the subparticle having an index of refraction below the index of refraction of the polymeric base is encapsulated air, vacuum or gas.

9. The composite particle according to claim 1 wherein the void is produced from a porogen.

10. The composite particle according to claim 1 wherein the composite particle has a diameter from about 0.5 to 75 microns.

11. The composite particle according to claim 1 wherein the subparticle having an index of refraction above the index of refraction of the polymeric base has an index of refraction from 1.65 to 3, makes up from 0.1 to 35% by weight of the composite particle and has a diameter from 20 to 800 nm, and the void having an index of refraction below the index of refraction of the polymeric base has an index of refraction from 1 to 1.4 and has a diameter from 50 to 800 nm.

12. The composite particle according to claim 11 wherein the void makes up from 1 to 8% by volume of the polymeric base and the subparticle having an index of refraction below the index of refraction of the polymeric particle makes up from 0.1 to 20% by weight of the composition.

13. A cosmetic composition comprising:
(i) a composite particle of claim 1; and
(ii) a cosmetically acceptable carrier.

14. The cosmetic composition according to claim 13 wherein the cosmetically acceptable carrier is an emulsion.

15. The cosmetic composition according to claim 13 wherein the composition comprises from 0.1 to 20% by weight of the composite particle.

16. A method for improving skin characteristics comprising the step of topically applying to skin the composition of claim 13.

17. The composite particle according to claim 1 wherein the other unsaturated monomers are selected from the group consisting of vinyl acetate monomers, acrylonitrile monomers, methacrylonitrile monomers, nitrogen containing ring compound unsaturated monomers, vinylaromatic monomers, ethylenic monomers, selected (meth)acrylic acid derivatives, and any combination thereof.

* * * * *